US00PP29071P2

(12) United States Plant Patent
Danziger

(10) Patent No.: US PP29,071 P2
(45) Date of Patent: Mar. 6, 2018

(54) ***BIDENS* PLANT NAMED 'DBIDBLAZGL'**

(50) Latin Name: *Bidens ferulifolia*
Varietal Denomination: DBIDBLAZGL

(71) Applicant: Gavriel Danziger, Beit Dagan (IL)

(72) Inventor: Gavriel Danziger, Beit Dagan (IL)

(73) Assignee: Danziger 'DAN' Flower Farm (IL)

( * ) Notice: Subject to any disclaimer, the term of this patent is extended or adjusted under 35 U.S.C. 154(b) by 0 days.

(21) Appl. No.: 15/530,223

(22) Filed: Dec. 12, 2016

(51) Int. Cl.
*A01H 5/02* (2006.01)

(52) U.S. Cl.
USPC ..... Plt./410

(58) Field of Classification Search
USPC ..... Plt./356.11
See application file for complete search history.

*Primary Examiner* — Annette H Para
(74) *Attorney, Agent, or Firm* — Cassandra Bright

(57) ABSTRACT

A new and distinct *Bidens* cultivar named 'DBIDBLAZGL' is disclosed, characterized by semi-trailing plant. Foliage is pinnate. Flowers are large, orange with yellow centers and typically have eight petals. The new variety is a *Bidens*, normally produced as an outdoor garden or container plant.

2 Drawing Sheets

Figure 1:
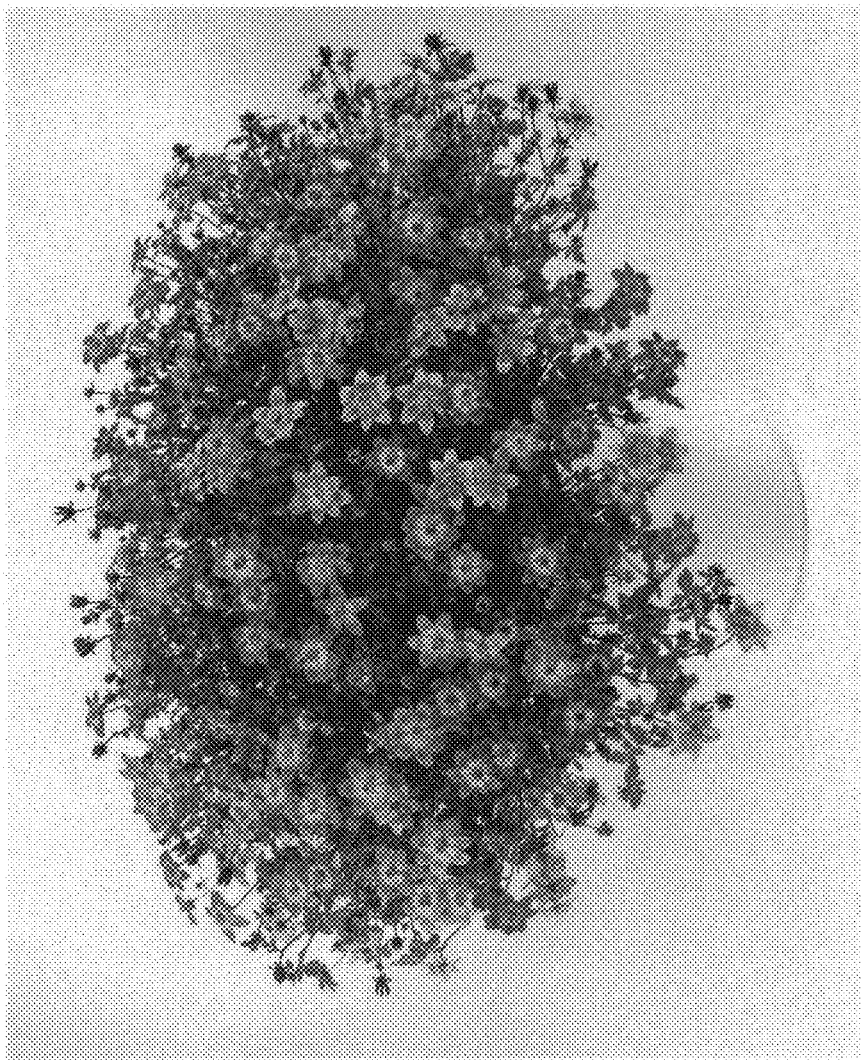

Latin name of the genus and species: *Bidens ferulifolia.*
Variety denomination: 'DBIDBLAZGL'.

BACKGROUND OF THE INVENTION

The new *Bidens* cultivar is a product of a planned breeding program conducted by the inventor, Gavriel Danziger in Moshav Mishmar Hashiva, Israel. The open pollination resulting in this new variety was made during September of 2014.

The seed parent is the unpatented, propriety variety referred to as *Bidens* 'cv.14-1864'. The pollen parent is unknown as it was an open pollination breeding program. The new variety was discovered in February 2015 by the inventor in a group of seedlings resulting from the 2014 open pollination, in a greenhouse in Moshav Mishmar Hashiva, Israel.

Asexual reproduction of the new cultivar 'DBIDBLAZGL' was first performed by vegetative cuttings during February of 2015, at a greenhouse in Moshav Mishmar Hashiva, Israel. Subsequent propagation by vegetative cuttings has shown that the unique features of this cultivar are stable and reproduced true to type in multiple successive generations.

SUMMARY OF THE INVENTION

The cultivar 'DBIDBLAZGL' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DBIDBLAZGL' These characteristics in combination distinguish 'DBIDBLAZGL' as a new and distinct *Bidens* cultivar:

1. Semi-trailing, compact growth habit.
2. Large flowers
3. 8-petaled flowers.
4. Orange flowers with a yellow center.
5. Pinnate foliage.

PARENT COMPARISON

Plants of the new cultivar 'DBIDBLAZGL' are similar to plants of the seed parent, most horticultural characteristics, however, plants of the new cultivar 'DBIDBLAZGL' differ in the following;

1. Plant habit of the new variety is semi-trailing, whereas the seed parent is vigorous, trailing plant.
2. New variety produces pinnate foliage, the parent variety has bipinnate foliage.
3. Parent has 5-petaled flowers.
4. Parent has yellow flowers, the new variety has orange flowers with a yellow center.

COMMERCIAL COMPARISON

Plants of the new cultivar 'DBIDBLAZGL' can be compared to the unpatented commercial variety *Bidens* 'DANYEL9'. These varieties are similar in most horticultural characteristics; however, 'DBIDBLAZGL' differs in the following:

1. The new variety has a semi-trailing growth habit, whereas the comparator has a mounded habit.
2. The new variety has pinnate foliage, the comparator has bipinnate foliage.
3. Comparator variety has extra-large yellow flowers, the new variety has large orange flowers with a yellow center.

Plants of the new cultivar 'DBIDBLAZGL' can also be compared to the unpatented commercial variety *Bidens* 'DANYEL10'. These varieties are similar in most horticultural characteristics; however, 'DBIDBLAZGL' differs in the following:

1. The new variety has single flowers, this comparator has semi-double flowers.
2. The new variety has pinnate foliage, the comparator has bipinnate foliage.

3. The comparator variety has yellow flowers, the new variety has orange flowers with a yellow center.

BRIEF DESCRIPTION OF THE PHOTOGRAPHS

The accompanying photograph in FIG. 1 illustrates in full color a typical plant of 'DBIDBLAZGL' grown in 13 cm pots outdoors in Moshav Mishmar Hashiva, Israel.

Figure 2:
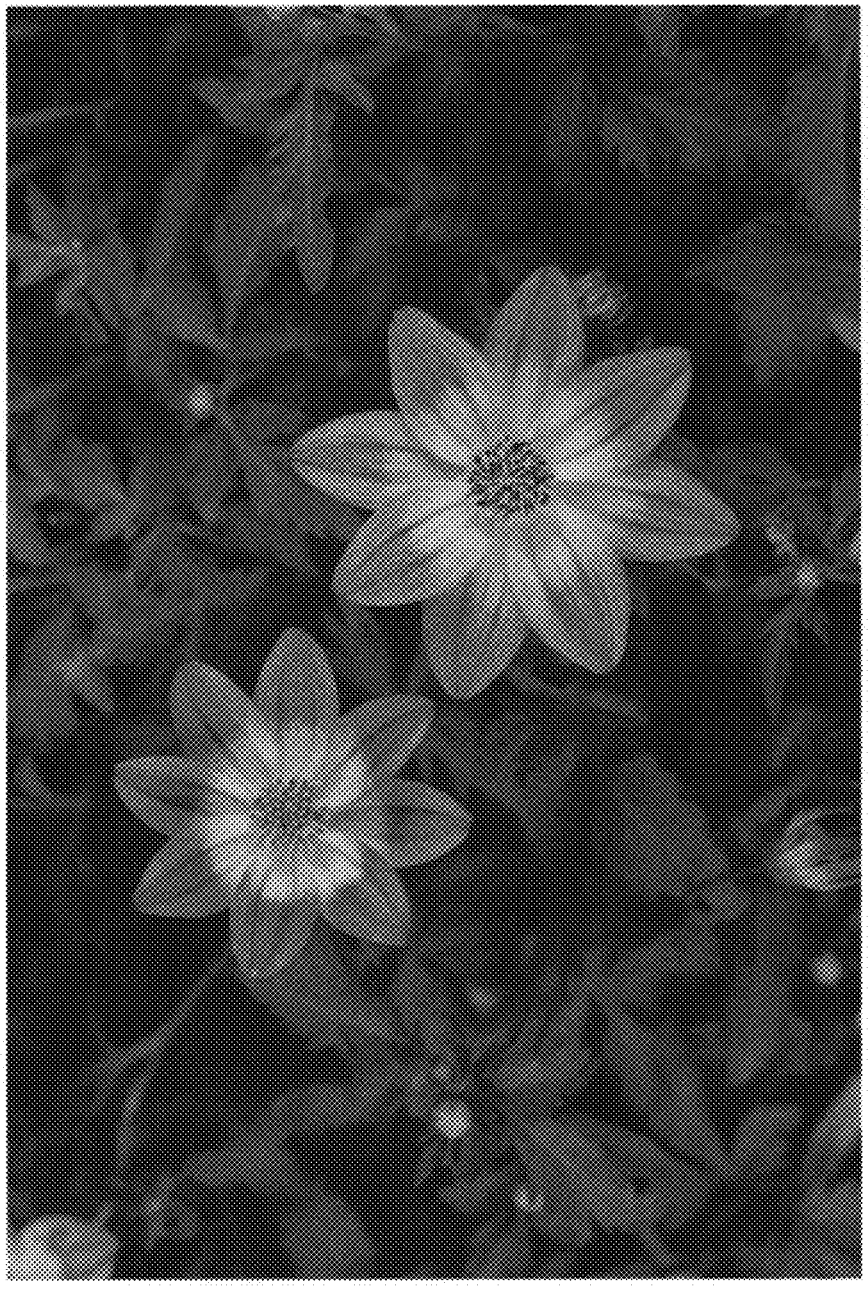

FIG. 2 illustrates in full color a close up view of flowers of 'DBIDBLAZGL'. Age of the plant photographed is approximately 3 months from a rooted cutting.

The photographs were taken using conventional techniques and although colors may appear different from actual colors due to light reflectance it is as accurate as possible by conventional photographic techniques.

DETAILED BOTANICAL DESCRIPTION

In the following description, color comparators are made to The Royal Horticultural Society Mini Colour Chart 2005 except where general terms of ordinary dictionary significance are used. The following observations and measurements describe 'DBIDBLAZGL' plants grown in a greenhouse and outdoors in Moshav Mishmar Hashiva, Israel, under natural lighting. Measurements were taken during April of 2016. The plants were approximately 60 days old from a rooted cutting in a 12 cm pot. The growing temperature ranged from approximately 20° C. to 35° C. during the days, 17° C. to 23° C. during the nights. Measurements and numerical values represent averages of typical plant types.

Botanical classification: *Bidens ferulifolia* 'DBIDBLAZGL'.

PROPAGATION

Time to initiate rooting: 10 to 14 days at approximately 20° C.

Root description: Fibrous. Tan to brown in color, not accurately measured with an R.H.S. chart.

PLANT

Growth habit: Upright.
Height: Approximately 15 cm.
Plant spread: Approximately 35 cm.
Growth rate: Moderate.
Branching characteristics: Moderately well branched.
Length of lateral branches: Approximately 17 cm.
Diameter of lateral branches: Approximately 0.2 cm.
Texture of lateral branches: Glabrous.
Internodes length: Approximately 2.0 cm.
Strength of stem: Strong.
Color of lateral branches: Near Yellow-Green group 144B.
Angle of branches: Approximately 30°.
Number of Leaves per lateral branch: Approximately 20.

FOLIAGE

Leaf:
- *Arrangement*.—Opposite.
- *Average length*.—Approximately 4.5 cm.
- *Average width*.—Approximately 2.5 cm.
- *Shape of blade*.—Pinnate.
- *Apex*.—Acute.
- *Base*.—Cuneate.
- *Margin*.—Dentate.
- *Texture of top surface*.—Glabrous.
- *Texture of bottom surface*.—Glabrous.
- *Appearance top surface*.—Matte.
- *Appearance bottom surface*.—Matte.
- *Leaf internode length*.—Approximately 0.5 cm.
- *Color*.—Young foliage upper side: Near Green 137A. Young foliage under side: Near Yellow-Green 147B. Mature foliage upper side: Near Green 137B. Mature foliage under side: Near Yellow-Green 147C.
- *Venation*.—Type: Pinnate. Venation color upper side: Near Green 137C. Venation color under side: Near Yellow-Green 147B.

Petiole:
- *Length*.—1.0 cm.
- *Diameter*.—0.1 cm.
- *Pubescence*.—Slightly pubescent.
- *Color*.—Near Yellow-Green 147B.

FLOWER

Bloom period: Year-round.

Bud:
- *Bud shape*.—Ovate.
- *Bud length*.—Approximately 1.0 cm.
- *Bud diameter*.—Approximately 0.6 cm.
- *Bud color*.—Near RHS Greyed-Orange 173A.

Inflorescence:
- *Form*.—Solitary capitulum.

Flower:
- *Diameter of entire flower*.—Approximately 3.5 cm.
- *Depth of flower*.—Approximately 1.5 cm.
- *Diameter of disc*.—Approximately 0.6 cm.
- *Depth of disc*.—Approximately 0.6 cm.

Ray florets:
- *Number of ray florets*.—Average of 8.
- *Length*.—Approximately 1.5 cm.
- *Width*.—Approximately 0.8 cm.
- *Apex shape*.—Acute.
- *Margin*.—Entire.

Color:
- *Ray florets*.—Upper surface at first opening: Near RHS Greyed-Orange 175 A with center Yellow-Orange 17 A. Upper surface at maturity: Near RHS Greyed-Orange 172 B with center Yellow-Orange 17 B. Upper surface at fading: Near RHS Greyed-Orange 172 C with center Yellow-Orange 17 C. Under surface at first opening: Near RHS Greyed-Orange N 172 A. Under surface at maturity: Near RHS Greyed-Orange N 172 C with center Yellow-Orange 17 C. Under surface at fading: Near RHS Greyed-Orange 168 C with center Yellow-Orange 17 D.
- *Disc florets*.—Number of Disc Florets: Approximately 40. Length: Approximately 0.7 cm. Width: Approximately 0.1 cm. Shape: Linear. Margin: Entire.
- *Color*.—At first opening: Near Yellow-Orange 17A. At maturity: Near Yellow-Orange 17B. At fading: Near Yellow-Orange 17B.

Fragrance: None.

Phyllaries/involucral bracts:
- *Number*.—8.
- *Sepal length*.—Approximately 0.6 cm.
- *Sepal width*.—Approximately 0.1 cm.
- *Sepal texture*.—Glabrous.
- *Apex shape*.—Acute.
- *Margin*.—Entire.

*Color*.—Near Yellow-Green 144B.

Peduncle:

*Pedicel length*.—Approximately 4.0 cm.

*Pedicel diameter*.—Approximately 0.2 cm.

*Angle*.—Approximately 30° from center of whorl.

*Color*.—Near Yellow-Green 144A.

*Strength*.—Flexible.

*Pedicel texture*.—Glabrous.

REPRODUCTIVE ORGANS

Disc florets:

Androecium:

*Stamens*.—5.

*Anther shape*.—Rounded.

*Anther length*.—Approximately 0.1 cm.

*Anther color*.—Near RHS Greyed-Orange 165A.

*Pollen quantity*.—Sparse.

Gynoecium:

*Pistil number*.—1.

*Pistil shape*.—Linear.

*Pistil length*.—Approx. 0.4 cm.

*Style length*.—Approx. 0.3 cm.

*Style color*.—Near Yellow-Green 154B.

*Stigma shape*.—Two-lobed.

*Stigma color*.—Near Yellow-Orange 17B.

*Ovary diameter*.—0.1 cm.

*Ovary color*.—Near Yellow-Green 144C.

Ray florets: No reproductive structures present.

OTHER CHARACTERISTICS

Seeds and fruits:

*Shape*.—Needle-like.

*Color*.—Near RHS Brown 200A.

*Size*.—Approximately 0.6 cm long, 0.1 cm wide.

Disease/pest resistance: Neither resistance nor susceptibility to normal diseases and pests of *Bidens* has been observed.

Temperature tolerance: Temperature range: 5° C. to 40° C.

Drought tolerance: Not tolerant to drought.

What is claimed is:

1. A new and distinct cultivar of *Bidens* plant named 'DBIDBLAZGL' as herein illustrated and described.

* * * * *